United States Patent [19]

Segers et al.

[11] Patent Number: 5,383,324
[45] Date of Patent: Jan. 24, 1995

[54] METHOD FOR MANUFACTURING AND STORING STABLE BICARBONATE SOLUTIONS

[75] Inventors: Alain Segers, Huizingen; Dirk Faict, Assenede; Annick Duponchelle, Bruxelles; Jean-Pierre Hartman, Rode; Francesco Peluso, Heverlee, all of Belgium

[73] Assignee: Baxter International Inc., Deerfield, Ill.

[21] Appl. No.: 52,260

[22] Filed: Apr. 23, 1993

[51] Int. Cl.[6] .................. B65B 29/06; B65B 55/18
[52] U.S. Cl. ........................ 53/425; 53/431; 53/434; 53/474; 206/524.1
[58] Field of Search .......... 53/431, 434, 474, 425, 53/240, 239, 237; 206/524.1

[56] References Cited

U.S. PATENT DOCUMENTS

| | | | |
|---|---|---|---|
| 3,878,664 | 4/1975 | Zinke | 53/474 X |
| 4,372,100 | 2/1983 | Miller et al. | 53/474 X |
| 4,396,383 | 8/1993 | Hart | 604/56 |
| 4,397,392 | 8/1983 | Ronck et al. | 53/474 X |
| 4,465,488 | 8/1984 | Richmond et al. | 604/414 |
| 4,489,535 | 12/1984 | Veltman | 53/431 |
| 4,584,176 | 4/1986 | Oliver et al. | 422/41 |
| 4,959,175 | 9/1990 | Yatzidis | 252/364 |
| 5,092,838 | 3/1992 | Faict et al. | 604/27 |

FOREIGN PATENT DOCUMENTS

| | | |
|---|---|---|
| 0209607 | 1/1987 | European Pat. Off. . |
| 0278100 | 6/1988 | European Pat. Off. . |
| 0399549 | 11/1990 | European Pat. Off. . |
| 0399918 | 11/1990 | European Pat. Off. . |
| 0417478 | 3/1991 | European Pat. Off. . |
| 0437274 | 7/1991 | European Pat. Off. . |
| 0481257 | 4/1992 | European Pat. Off. . |

OTHER PUBLICATIONS

"Peritoneal Dialysis Using Bicarbonate-Containing Solution Sterilized by Ultrafiltration", Manahan et al, Int. J. Artif. Org., No. 8 1991.
"Use of an Artificial Kidney", Murphy et al, 1952.
"Bicarbonate-Buffered Peritoneal Dialysis" Ing, et al, Int. Journal of Artificial Organs, vol.8, No. 3, 1985.

Primary Examiner—James F. Coan
Attorney, Agent, or Firm—Charles R. Mattenson; Thomas S. Borecki; Robert M. Barrett

[57] ABSTRACT

A method and device for stabilizing and storing bicarbonate solutions is provided. In an embodiment, a device is provided having a container and carbon-dioxide generating substances that include a solid material which upon contact with water generates carbon-dioxide gas. The device may be packaged together with the bicarbonate or in a separate overpouch. The present invention also provides a method for the stabilization of bicarbonate solutions utilizing a means that generates high pressure carbon dioxide.

18 Claims, 1 Drawing Sheet

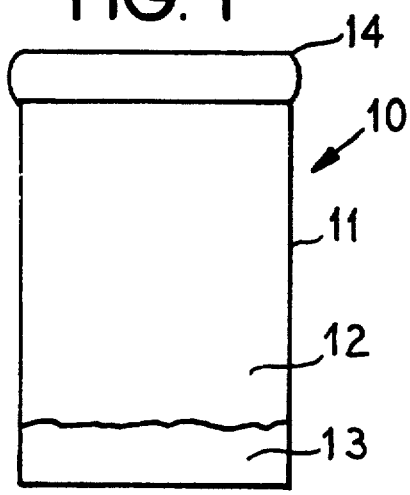
FIG. 1
FIG. 2
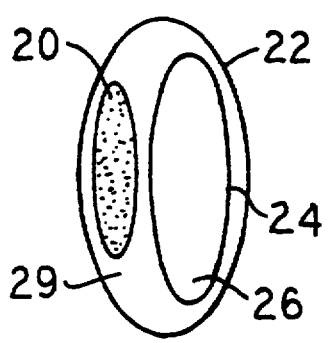
FIG. 3
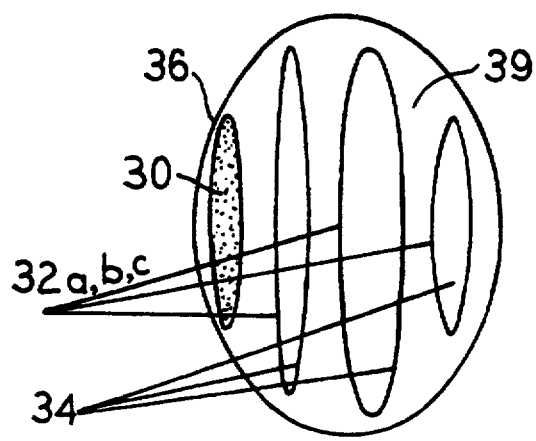
FIG. 4
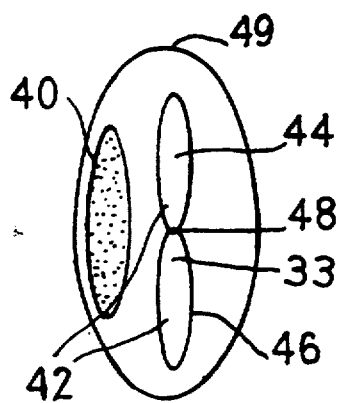
FIG. 5
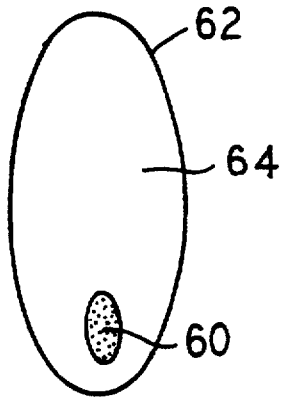

METHOD FOR MANUFACTURING AND STORING STABLE BICARBONATE SOLUTIONS

BACKGROUND OF THE INVENTION

The present invention relates generally to peritoneal dialysis. More specifically, the present invention relates to manufacturing and storing bicarbonate peritoneal dialysis solutions.

The use of dialysis to support a patient whose renal function has decreased to the point where the kidneys no longer sufficiently function is known. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, certain inherent disadvantages are present with hemodialysis.

To overcome the disadvantages associated with hemodialysis, peritoneal dialysis was developed. Peritoneal dialysis utilizes the patient's own peritoneum as a semipermeable membrane. The peritoneum is the membranous lining of the body cavity that due to the large number of blood vessels and capillaries is capable of acting as a natural semipermeable membrane.

In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows a proper acid-base, electrolyte and fluid balance to be returned to the blood. The dialysis solution is simply drained from the body cavity through the catheter.

Besides the removal of metabolism products, one of the most important problems of every kidney replacement therapy, such as hemodialysis and peritoneal dialysis, lies in the correction of metabolic acidosis. For this reason, the dialysis solutions used in each of these processes contain a buffer.

Three common buffers often used in dialysis solutions are bicarbonate, lactate, and acetate. While initially bicarbonate was the primary buffer used in dialysis solutions, over time lactate and acetate were substituted for bicarbonate. This was due to the difficulty in preparation and storage of bicarbonate-buffered dialysis solutions. Lactate and acetate buffers were found to provide greater stability in use over the previous bicarbonate-buffered solutions. See European Patent Application 90109963.0.

However, since bicarbonate ions provide advantages over acetate or lactate ions, bicarbonate is again surfacing as the primary buffer used in dialysis solutions. Tests conducted in recent years indicate patients exhibit a better tolerance for bicarbonate dialysis solutions. Further, certain treatments require sterile dialysis solutions containing bicarbonate, calcium and magnesium.

For example, one may have to dialyze a uremic patient who has developed hypotension and lactate acidosis. In such a patient, the lactate or acetate in conventional dialysates may not be metabolized to bicarbonate because of tissue hypoxia, and acidosis may be further worsened because bicarbonate is removed during dialysis. Using bicarbonate-containing dialysates in such a patient will add bicarbonate to the blood and also remove lactate. For these reasons, some researchers have recommended bicarbonate-buffered dialysis as adjunctive treatment for severe lactic acidosis. T. S. Ing. et al, *Bicarbonate—Buffered Peritoneal Dialysis*, The International Journal of Artificial Organs, Volume 8, No. 3, P.121 (1985).

Another potential application is with respect to patients who experience abdominal pain or discomfort when conventional acid- or lactic-buffered dialysates are infused. The abdominal pain may be related to the unphysiologically high acidity of acetate- and lactic-buffered dialysates. Conceivably, bicarbonate-buffered dialysate, with its more physiologic pH, might decrease the incidence of such symptoms. Id.

The use of medical bicarbonate solutions for injection or for dialysis treatment is known. However, due to the difficulty in preparation and storage of these solutions, a vast array of literature is dedicated to attempts to remedy the stability problem of bicarbonate solutions. Three main problems need to be addressed when manufacturing medical bicarbonate solutions.

First, in solution bicarbonate is in equilibrium with $CO_2$ gas, which easily escapes from the solution. As a result, carbonate, a potential irritant, may form and the pH of the solution is thereby increased. To avoid these phenomena from occurring, the bicarbonate can be stored in a powder form until just before use as described in U.S. Pat. No. 4,489,535 and Jonsson et al, European Patent Application 0278100 for machine-controlled dialysis.

Alternatively, an impermeable barrier can be used to protect the solution. Or, for hemodialysis, the $CO_2$ content of the solution can be controlled as described in Murphy et al, *Use of An Artificial Kidney*, J Lab. Clin. Med., Volume 40, pp. 436–444 (1952). U.S. Pat. No. 4,584,176 and European Patent No. 0,209,607 describe controlling the $CO_2$ content of the solution. Moreover, the addition of buffers such as histidine or glycylglycine may further stabilize the bicarbonate solution. See, U.S. Pat. Nos. 5,092,838 and 4,959,175.

Second, bicarbonate solutions for injection and for dialysis generally contain calcium and/or magnesium ions. In the presence of bicarbonate, these ions form calcium carbonate and magnesium carbonate respectively, which easily precipitate from the solution, especially at a pH above 7.5. To remedy this problem, bicarbonate solutions are often made from concentrates, ranging from slightly concentrated, two-fold or less, to much more concentrated solutions. Bicarbonate on the one hand and calcium and/or magnesium on the other hand are included in separate concentrates. These concentrates are then mixed to obtain a ready to use solution. Alternatively, the concentrates are mixed and diluted.

In order to avoid the precipitation of carbonate salts, the bicarbonate concentrate is acidified when manufactured. Alternatively, the bicarbonate concentrate is mixed with an acid or acidified concentrate, either before or after dilution if dilution is needed. Acidification can be achieved with an organic (acetic acid, lactic acid), inorganic acids (hydrochloric acid) or with carbon dioxide. Ing et al., *Bicarbonate—Buffered Peritoneal Dialysis*, Volume 8, No. 3, p. 121 (1985). A series of machines have been proposed to assure appropriate mixing, see U.S. Pat. No. 4,489,535.

While the preparation of concentrates in separated containers initially prevents carbonate precipitation, immediate mixing of the concentrates results in carbonate precipitation. This subsequent precipitation leads to disturbances of the dialysis operation. To remedy this problem, technicians have been forced to rinse all tube lines at regular intervals with acid. Naturally, this technique results in added expense in terms of technician time and the additional cost of the acid needed.

Likewise, the dilution of the concentrated solutions to prevent carbonate precipitations has inherent disadvantages. The dilution of the solutions does not completely obviate the precipitation problem and represents an additional step. Further diluted concentrates may not adequately correct the acidosis of patients.

Third, bicarbonate solutions for injection and for certain types of dialysis need to be sterile. Either sterile filtration or steam sterilization may be used. When steam sterilization is used, many substances cannot be autoclaved together with bicarbonate. Therefore, the solution must be sterilized in at least two parts: one part containing the bicarbonate; and another part containing the incompatible substance(s), such as dextrose. In practice, two containers can be used, or alternatively, multi-compartment containers can be used. See U.S. Pat. Nos. 4,396,383 and 4,465,488.

Current procedures and preparations do not provide an adequate means to stabilize bicarbonate solutions that allow also for sterilization of such solutions. There therefore remains a need for an improved method for manufacturing and storing bicarbonate solutions.

SUMMARY OF THE INVENTION

The present invention provides devices and methods for stabilizing bicarbonate solutions. Pursuant to the present invention, carbon dioxide gas is used to stabilize bicarbonate solutions.

In an embodiment of the present invention, a device that generates carbon dioxide gas is used to stabilize the bicarbonate solutions. The device can be packaged in an overpouch that surrounds a bicarbonate container that is filled with a bicarbonate solution. In this embodiment, the bicarbonate container would be sufficiently gas permeable to allow $CO_2$ generated by the device to enter the container. Alternatively, the device can be directly located in the bicarbonate container filled with bicarbonate solution. Preferably, the device has an interior compartment that houses a material that upon contact with water generates carbon dioxide gas.

Preferably, the $CO_2$ is generated during a reaction wherein a stronger acid displaces a weaker acid. In an embodiment, the solid material consists of a bicarbonate and an acid either in powder or granular form. Alternatively, the solid material consists of a carbonate and an acid both in powder or granular form.

The present invention also provides methods for stabilizing bicarbonate solutions. Pursuant to the method, a $CO_2$ pressure of at least 80 mm Hg (determined at 37° C.) is maintained in the bicarbonate solution.

For example, in an embodiment of the method, first, a bicarbonate solution is placed in a container that is constructed from a material that allows carbon dioxide to pass therethrough. The bicarbonate container is then packaged in a second container or overpouch. The bicarbonate solution is stabilized by means that generates carbon dioxide at a pressure of greater than or equal to 80 mm Hg (determined at 37° C.) in the overpouch.

In another embodiment, a bicarbonate solution is placed in a container having an exterior that is impermeable to water and carbon dioxide. Then, a pressure of at least 80 mm Hg is maintained in the container. For example, the pressure can be achieved by a device that generates carbon dioxide that is located in the bicarbonate container.

It is an advantage of the present invention to provide a method for stabilizing bicarbonate solutions to be used in medical procedures.

Another advantage of the present invention is that it provides a cost effective device for stabilizing bicarbonate solutions that can be used before, during, or after steam sterilization in peritoneal dialysis systems.

A further advantage of the present invention is that it provides a system and/or method that can be used to stabilize both solutions for use either in continuous ambulatory peritoneal dialysis (CAPD) or automated peritoneal dialysis (APD).

Additional features and advantages of the present invention are described in, and will be apparent from, the detailed description of the presently preferred embodiments as well as the drawings.

BRIEF DESCRIPTION OF THE DRAWINGS

FIG. 1 illustrates a front elevational view of an embodiment of a device for generating carbon dioxide of the present invention.

FIG. 2 illustrates a cross-sectional view of a system pursuant to the present invention including a bicarbonate container, a device for the generation of carbon dioxide, and an overpouch container.

FIG. 3 illustrates a cross-sectional view of a further embodiment of a system of the present invention including a device for the generation of carbon dioxide packaged together with a plurality of bicarbonate solution containers, all of which are located in an overpouch.

FIG. 4 illustrates a cross-sectional view of a further embodiment of a system of the present invention including a device for the generation of carbon dioxide packaged together in an overpouch with a multi-chamber container containing a complete dialysis solution.

FIG. 5 illustrates a cross-sectional view of a still further system of the present invention including a device for the generation of carbon dioxide located within a bicarbonate solution container.

DETAILED DESCRIPTION OF THE PRESENTLY PREFERRED EMBODIMENTS

The present invention provides an improved method for storing and stabilizing a bicarbonate solution. Pursuant to the present invention, carbon dioxide is used to stabilize the bicarbonate solution.

In an embodiment, the present invention provides a device that produces carbon dioxide for stabilizing bicarbonate solutions. The device can be located within a container that contains the bicarbonate solution. Alternatively, the device can be located within an overpouch that surrounds the container filled with a bicarbonate solution. As discussed in detail below, pursuant to the present invention, other means can be used, aside from the device, to generate the necessary carbon dioxide.

What is important is that pursuant to the present invention, carbon dioxide is used to stabilize the solution. Indeed, in contrast to the belief in the prior art, the inventors have found that carbon dioxide pressures of 80 mm Hg (determined at 37° C.) and greater can be used to stabilize the bicarbonate solution. Heretofore, it was believed that these pressures would create a CAPD or APD solution that was hazardous to the health of the patient when infused. In contrast, the inventors have found that such pressures are not hazardous, but rather, provide a means for stabilizing bicarbonate.

Referring now to the Figures, FIG. 1 illustrates a front elevational view of an apparatus for producing carbon dioxide made in accordance with the present invention. The device 10 includes an exterior body 11. The exterior body 11 can be made of any rigid or flexible material that is permeable to water and carbon dioxide. In an embodiment, the exterior body 11 is made of high density polyethylene. Alternatively, the exterior body 11 can be made of a material impermeable to water and $CO_2$ and instead has small pores. The small pores allow for the transport of water vapors and $CO_2$. While the illustrated embodiment of the device 10 is rectangular in shape, the precise shape of the device 10 is not critical to the invention.

The exterior body 11 defines an interior compartment 12. The interior compartment 12 preferably houses a solid material 13. The solid material 13 is chosen so that upon contact with water or water vapor it generates carbon-dioxide gas. The generation occurs during a chemical reaction in which $CO_2$ is generated as a stronger acid displaces a weaker acid.

To this end, the solid material 13 may consist of a blend of bicarbonate in powder or granular form and an acid in powder or granular form. In an embodiment, the bicarbonate is sodium bicarbonate. Alternatively, instead of a bicarbonate, the solid material 13 may consist of a carbonate in powder or granular form with an acid in powder or granular form. In an embodiment, the carbonate is sodium carbonate.

A wide range of acids can be used in combination with the bicarbonate or carbonate to produce carbon dioxide. In an embodiment, the acid is a carboxylic acid. In a preferred embodiment, the acid is a carboxylic acid chosen from the group consisting of lactobionic acid, succinic acid, or citric acid. Upon contact with water, this blend will generate $CO_2$ gas.

In the illustrated embodiment, the device 10 includes a cover 14. The cover 14 allows for the easy filling of the device 10. Preferably, the cover 14 is made of the same material as the exterior body 11. In an embodiment, the cover 14 is made of high density polyethylene.

In use, the amount of solid material 13 within the device 10 determines the amount of carbon dioxide that is generated by the device 10. Further, the amount of solid material 13 that is needed is also dependent on the amount of carbon dioxide that will escape through the container housing the device 10.

As stated above, the solid material 13 generates carbon dioxide upon contact with water. Since the device 10 is permeable to water, water vapor or steam will enter the device 10, especially during steam sterilization of the solution containers and start the carbon dioxide generation. Moreover, if necessary, water can be added to the device 10 to facilitate the generation of carbon dioxide.

By way of example, and not limitation, in an embodiment, ten grams of sodium bicarbonate is placed within the device 10. The ten grams of sodium bicarbonate is enough to generate two liters of carbon dioxide and will therefore, in the systems set forth in FIGS. 2–5, stabilize a bicarbonate solution for several months to years. Once all of the carbon dioxide has been generated, the carbon dioxide will still stabilize the bicarbonate solution, provided it is not lost through the container housing the solution. Naturally, the rate of carbon dioxide generation can be varied and depends on the organic acid used, the ratio of bicarbonate to organic acid, the humidity within the container and the temperature and size of the particles, if granules are used. These are all matters that can be considered in constructing the device.

FIG. 2 illustrates a cross-sectional view of an embodiment of the device 20 made in accordance with the present invention packaged together in an overpouch 22 with a container 24 that includes a bicarbonate solution 26. The bicarbonate container 24 can be made of any material that is highly permeable to carbon dioxide. For example, the bicarbonate container 24 can be made of a polyolefin (for example, high density polyethylene) or polyvinylchloride.

The overpouch or second container 22 surrounds both the device 20 and the bicarbonate container 24. The overpouch 22 is made of any material with low permeability to gas and specifically, carbon dioxide. The low permeability of the overpouch 22 prevents $CO_2$ from escaping and thereby maintains a $CO_2$ pressure within an interior of the overpouch 22 and therefore, within the bicarbonate container 24. In an embodiment, the overpouch 22 comprises a laminate that includes a layer of aluminum foil. However, any low permeable material can be used.

In use, $CO_2$ gas is generated by the device 20 as water, typically from steam sterilization entering the device 20. This creates a certain $CO_2$ pressure in the interior 29 of the overpouch 22. The $CO_2$ pressure within the interior 29 of the overpouch 22, due to the permeability of the bicarbonate container 24, is thereby established also in the bicarbonate container 24. This $CO_2$ pressure stabilizes the bicarbonate solution 26.

FIG. 3 illustrated another embodiment of a system for stabilizing bicarbonate solutions. In the illustrates system, a device 30 made in accordance with the present invention is packed together with bicarbonate containers 32a, b, and c filled with bicarbonate solutions 34. However, in contrast to the system in FIG. 2, in FIG. 3, a plurality of bicarbonate containers 32a, b, and c are used. The device 30 and the plurality of bicarbonate containers 32a, b, and c are again enclosed by an overpouch 36.

Again, the device 30 generates $CO_2$ after steam sterilization or some other means for adding water to the interior of the device 30 to create a $CO_2$ pressure within the interior 39 of the overpouch 36. This creates a defined $CO_2$ pressure in the containers 32a, b, and c.

For example, in an embodiment, the solution contained in the container 24 or the container 32a, b, or c is sterilized by filtration and has the following composition: 15.0 to about 45.0 (mmol/L) bicarbonate; 90.0 to about 110.0 (mmol/L) chloride; 90.0 to 142.0 (mmol/L) sodium; 0.0 to about 2.0 (mmol/L) calcium; 0.0 to about 1.0 (mmol/L) magnesium; 0.0 to about 3.0 (mmol/L) potassium; 0.0 to about 4.0% amino acids; 0.0 to about 4.0% peptides; 0.0 to about 4.0% glycerol; 0.0 to about 5.0% dextrose; and 0.0 to about 10.0% dextrose polymers.

As a second example, in an embodiment, the solution of bicarbonate (30–90 mmol/L), sodium (180–284 mmol/L), potassium (0–6 mmol/L), and chloride (counter ion) contained in the container 24 or the container 32a, b, or c is mixed aseptically with a solution containing dextrose (0–10%), dextrose polymers (0–20%), amino acids (0–8%), peptides (0–8%), calcium (0–4 mmol/L), magnesium (0–2 mmol/L), chloride (counter ion) in a 1 to 1 proportion.

The subsequent peritoneal dialysis solution is particularly suited for automated peritoneal dialysis and has the following composition: 15.0 to about 45.0 (mmol/L) bicarbonate; 90.0 to about 110.0 (mmol/L) chloride; 90.0 to 142.0 (mmol/L) sodium; 0.0 to about 2.0 (mmol/L) calcium; 0.0 to about 1.0 (mmol/L) magnesium; 0.0 to about 3.0 (mmol/L) potassium; 0.0 to about 4.0% amino acids; 0.0 to about 4.0% peptides; 0.0 to about 4.0% glycerol; 0.0 to about 5.0% dextrose; and 0.0 to about 10.0% dextrose polymers.

FIG. 4 illustrates a cross-sectional view of another system made in accordance with the present invention. A device 40 is packaged together with a multi-chamber container 42. The multi-chamber container 42 has an upper chamber 44 and a lower chamber 46.

In an embodiment, the multi-chamber container 42 has a frangible seal 48 between the upper chamber 44 and the lower chamber 46. Opening the frangible seal 48 provides fluid communication between the upper chamber 44 and the lower chamber 46. The multi-chamber 42 houses at least two non-compatible solutions that after mixture will result in a ready-to-use dialysis solution. An example of the multi-chambered container 42 is set forth in U.S. patent application Ser. No. 08/006,339, the disclosure of which is incorporated herein by reference.

Although all of the systems disclosed herein are designed to be used for any medical procedure requiring bicarbonate, and especially peritoneal dialysis, the embodiment illustrated in FIG. 4 is conveniently used for CAPD. To this end, in an embodiment, the upper chamber 44 contains calcium chloride and magnesium chloride, whereas the lower container 46 contains bicarbonate. In a preferred embodiment, the upper chamber 44 can further include sodium chloride, potassium chloride, dextrose and dextrose polymers. Likewise, the lower chamber 46 can further include sodium chloride, potassium chloride, amino acids, peptides and glycerol.

For example, in an embodiment, when the solution contained in the upper chamber 44 is mixed with the solution contained in the lower chamber 46, the subsequent peritoneal dialysis solution has the following composition: 15.0 to about 45.0 (mmol/L) bicarbonate; 90.0 to about 110.0 (mmol/L) chloride; 90.0 to 142.0 (mmol/L) sodium; 0.0 to about 2.0 (mmol/L) calcium; 0.0 to about 1.0 (mmol/L) magnesium; 0.0 to about 3.0 (mmol/L) potassium; 0.0 to about 4.0% amino acids; 0.0 to about 4.0% peptides; 0.0 to about 4.0% glycerol; 0.0 to about 5.0% dextrose; and 0.0 to about 10.0% dextrose polymers.

Since the lower chamber 46 contains the bicarbonate solution, at least the lower portion of the multi-chamber container 42 is made of a material permeable to carbon dioxide. Unlike the solution in the lower chamber 46, the solution in the upper chamber 44 does not have to be stabilized by carbon dioxide. Therefore, the upper chamber 44 can be made of any material. However, for ease of convenience, the upper chamber 44 can be constructed from the same material as the lower chamber 46. Similar to the systems in FIGS. 2 and 3, the device 40 and the multi-chamber container 42 is surrounded by an overpouch 49.

FIG. 5 illustrates a cross-sectional view of a still further system. In the system, a device 60 made in accordance with the present invention is located directly within the container 62. The container 62 is designed to house a bicarbonate solution 64.

Unlike the prior embodiments, the container 62 of FIG. 5 is made of a material that has low permeability to water and carbon dioxide. Thus, the bicarbonate solution in the container 62 will activate the device 60. Carbon dioxide will be generated directly in the container 62 stabilizing the bicarbonate solution contained therein.

The devices of the present invention can be used for stabilizing the bicarbonate solution during manufacturing and/or storage. The device of the present invention can be used before, during, or after steam sterilization. Preferably, the bicarbonate solutions are sterilized by steam sterilization as the last step of a manufacturing process. Afterwards, the solutions are stored in warehouses or at a patient's home. The steam sterilization presents extreme conditions and solutions may be stabilized by a carbon dioxide over-pressure in the autoclave. The device can then be used for stabilization during storage alone.

Moreover, it is also possible to do the reverse: use a device to create high carbon dioxide pressures during manufacturing, and then keep the product sealed under high carbon dioxide pressure (without the use of the device). Contrary to prior beliefs, the use of high carbon-dioxide pressure does not present health problems.

Pursuant to the present invention, high pressure carbon-dioxide may be used to stabilize bicarbonate solutions. High pressure encompasses pressures of at least 80 mm Hg and, if desired, more than 120 mm Hg. As stated above, the devices of the present invention can adequately provide such high pressures. However, the present invention is intended to also cover other means that generate carbon-dioxide at such pressures. For example, carbon dioxide can merely be fed in an overpouch and the overpouch that surrounds the container is then sealed.

As stated above, the device of the present invention can be used for both APD and CAPD. The ready-to-use bicarbonate solution of the present invention can be used for the treatment of acute and chronic renal failure and allows a better treatment of acidosis than currently available solutions. Further, the bicarbonate solution of the present invention provides metabolic benefits and improves cardiovascular status.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for stabilizing bicarbonate solutions, the method comprising the steps of:

housing a bicarbonate solution in a container made of a material permeable to carbon dioxide, wherein the container allows carbon dioxide to pass therethrough and further wherein the container is housed in an overpouch; and stabilizing the bicarbonate solution with a device consisting of a body housing a carbon-dioxide producing substance that includes a solid material which upon contact with water generates carbon dioxide.

2. The method of claim 1 wherein the device is located within the container.

3. The method of claim 1 wherein the device is located within the overpouch.

4. The method of claim 1 further comprising the step of:
steam sterilizing the container.

5. An assembly for storing bicarbonate solution for infusion into a patient, the assembly comprising:
a multi-chamber container for housing the bicarbonate solution, the multi-chamber container having a first chamber including bicarbonate and a second chamber including a second solution; and
a device for generating and maintaining a $CO_2$ pressure within the container, the device including a solid material which upon contact with water generates carbon-dioxide gas.

6. The assembly of claim 6 wherein the device maintains a partial carbon dioxide pressure in the container of at least 80 mm Hg (determined at 37° C.).

7. The assembly of claim 5 wherein the device is located within the container for housing bicarbonate solution.

8. The assembly of claim 7 wherein the container for housing bicarbonate solution is constructed from a material having low gas permeability.

9. The assembly of claim 5 further comprising:
an overpouch for surrounding the container for housing bicarbonate solution, the container being constructed from a material having a high gas permeability, the overpouch being constructed from a material having a low gas permeability, and the device being located within an interior defined by the overpouch.

10. The assembly of claim 9 including at least two containers within the overpouch.

11. A device for stabilizing a bicarbonate solution through the generation of carbon dioxide, the device comprising:
a container having an interior and including means for allowing fluid to enter the interior and at least carbon dioxide to exit the interior; and
carbon-dioxide generating substances located within the interior which upon contact with a fluid generates carbon-dioxide gas wherein the carbon-dioxide generating substances include a bicarbonate and an acid wherein the acid is an acid chosen from the group consisting of citric acid, lactobionic acid, or succinic acid.

12. The device of claim 11 wherein the means for allowing fluid to enter the interior includes constructing at least a portion of the container from a material having a high gas permeability to vapor.

13. The device of claim 11 wherein the device can generate and maintain in a closed environment a partial pressure of carbon dioxide of at least 80 mm Hg (determined at 37° C.).

14. A method for stabilizing bicarbonate solutions, the method comprising the steps of:
inserting a bicarbonate solution into a container; and
generating and maintaining a pressure (determined at 37° C.) of at least 80 mm Hg of $CO_2$ within the container wherein the pressure is generated by a device within the container.

15. The method of claim 14 wherein the container is made of a material permeable to carbon dioxide and the container is housed in an overpouch.

16. The method of claim 14 wherein the pressure is generated by a device located within the overpouch.

17. The method of claim 14 further comprising the step of:
steam sterilizing the container.

18. The method of claim 14 further comprising the step of:
mixing the bicarbonate solution with a second solution to obtain a ready to use medical solution, the second solution containing at least one component chosen from the group consisting of dextrose, dextrose polymers, peptides, and amino acids, the second solution not having been stabilized by carbon dioxide.

* * * * *